United States Patent [19]

Sasaki et al.

[11] Patent Number: 5,202,708
[45] Date of Patent: Apr. 13, 1993

[54] APPARATUS FOR PHOTOGRAPHIC RETROILLUMINATION IMAGE ON EYEGROUND

[75] Inventors: Kazuyuki Sasaki, Kanazawa; Nobuyuki Yano, Okazaki, both of Japan

[73] Assignee: Nidek Co., Ltd., Aichi, Japan

[21] Appl. No.: 744,059

[22] Filed: Aug. 9, 1991

[30] Foreign Application Priority Data

Aug. 10, 1990 [JP] Japan .................................. 2-213195

[51] Int. Cl.$^5$ ............................................. A61B 3/14
[52] U.S. Cl. .................................. 351/206; 351/211; 351/221; 354/62
[58] Field of Search ............... 351/205, 206, 211, 214, 351/221; 354/62

[56] References Cited

U.S. PATENT DOCUMENTS

| | | | |
|---|---|---|---|
| 4,019,813 | 4/1977 | Cornsweet et al. | 351/14 |
| 4,235,529 | 11/1980 | Kawase et al. | 351/14 |
| 4,523,821 | 6/1985 | Lang et al. | 351/214 |
| 4,711,540 | 12/1987 | Yoshino et al. | 351/214 |

Primary Examiner—Rodney B. Bovernick
Assistant Examiner—Hung Xuan Dang
Attorney, Agent, or Firm—Nikaido, Marmelstein, Murray & Oram

[57] ABSTRACT

A retroillumination image photographing apparatus of a crystalline lens in which an eye to be examined is projected by illumination light, and a crystalline lens is retroillumination with reflected light at an fundus of the illumination light, which includes: an alignment apparatus which aligns a photographing optical system of the retroillumination image photographing apparatus with a predetermined region of an eye to be examined; a storage apparatus which stores the position of the photographing optical system aligned by the alignment apparatus; and origin computing means which computes a specific region of the eye to be examined as an origin of an image pickup position of said photographing optical system based on the positional information of the storage apparatus; and detecting means which detects movement quantity of the image pickup position of the photographing optical system; and a display apparatus which displays the image pickup position of the photographing optical system based on the detection result of the detecting apparatus.

5 Claims, 3 Drawing Sheets

APPARATUS FOR PHOTOGRAPHIC RETROILLUMINATION IMAGE ON EYEGROUND

BACKGROUND OF THE INVENTION

The present invention relates to an apparatus for observing and examining lens opacity in human eyes, and more particularly to a retroillumination image photographing apparatus which is capable of obtaining a useful image of the lens.

A retroillumination image photographing apparatus in which an eye to be examined is projected to a light and the crystalline lens is retroilluminated with reflection at the fundus, thereby enabling it to observe the state of opacity in the crystalline lens has been heretofore well known.

In such a conventional retroillumination image photographing apparatus, alignment is performed by moving the apparatus main body in a longitudinal direction so as to photograph a position where an opacity area appears most clearly when the lens opacity is photographed.

With a conventional apparatus, however, it has not been possible to know exactly how deep the photographing position exists in the crystalline lens.

As a result, it has not been unable to photograph always at the same depth even for the same patient, which has interfered with the follow-up of chronological change in the progress of a cataract. Namely, there has been such a problem that pertinent evaluation cannot be made unless an error of the position of a photographed crystalline lens is taken into consideration when an opacity area is obtained repeatedly from the retroillumination image, thus being impossible to grasp a delicate change.

Further, the opacity areas are different depending on the types of cataract, and pertinent diagnosis such as on either nuclear cataract or cortical cataract (an opacity area exists in the cortex on the side of an iris or a vitreous body) could not be made.

Furthermore, it has not been possible to know the extent of opacity exactly even if a photograph is performed while changing the depth position.

SUMMARY OF THE INVENTION

It is an object of the present invention which has been made in view of drawbacks of above-mentioned conventional apparatus to provide a retroillumination image photographing apparatus which is capable of photographing of a retroillumination image with high reproducibility at a photographed position.

A first aspect of the present invention resides in a retroillumination image photographing apparatus of a crystalline lens in which an eye to be examined is projected by illumination light, and a crystalline lens is retroilluminated with reflected light at a fundus of the illumination light, comprising:

alignment means which aligns a photographing optical system of the retroillumination image photographing apparatus with a predetermined region of an eye to be examined;

storage means which stores the position of the photographing optical system aligned by the alignment means;

origin computing means which computes a specific region of the eye to be examined as an origin of an image pickup position of the photographing optical system based on the positional information of the storage means;

detecting means which detects movement quantity of the image pickup position of the photographing optical system; and display means which displays the image pickup position of the photographing optical system based on the detection result of the detecting means.

A second aspect of the present invention resides in a retroillumination image photographing apparatus characterized in that the alignment means which aligns a photographing optical system with a predetermined region of an eye to be examined set forth in the first aspect consists of a projection optical system which projects onto a cornea in order to form an image reflected at the cornea, an observation system for observing the image reflected at the cornea, and a sliding mechanism which moves the retroillumination image photographing optical system in an optical axis direction, and that alignment is made by adjusting so that the image reflected at the cornea and the photographing optical system have a predetermined positional relationship.

DESCRIPTION OF THE PREFERRED EMBODIMENTS

An embodiment of the present invention will be described hereinafter with reference to the drawings.

The present embodiment is an apparatus for photograph of the anterior segment of an eye including also an optical system for photographing a slit section image and a retroillumination image based on Scheinpfug's principles.

Construction of Optical System

Figure 1:
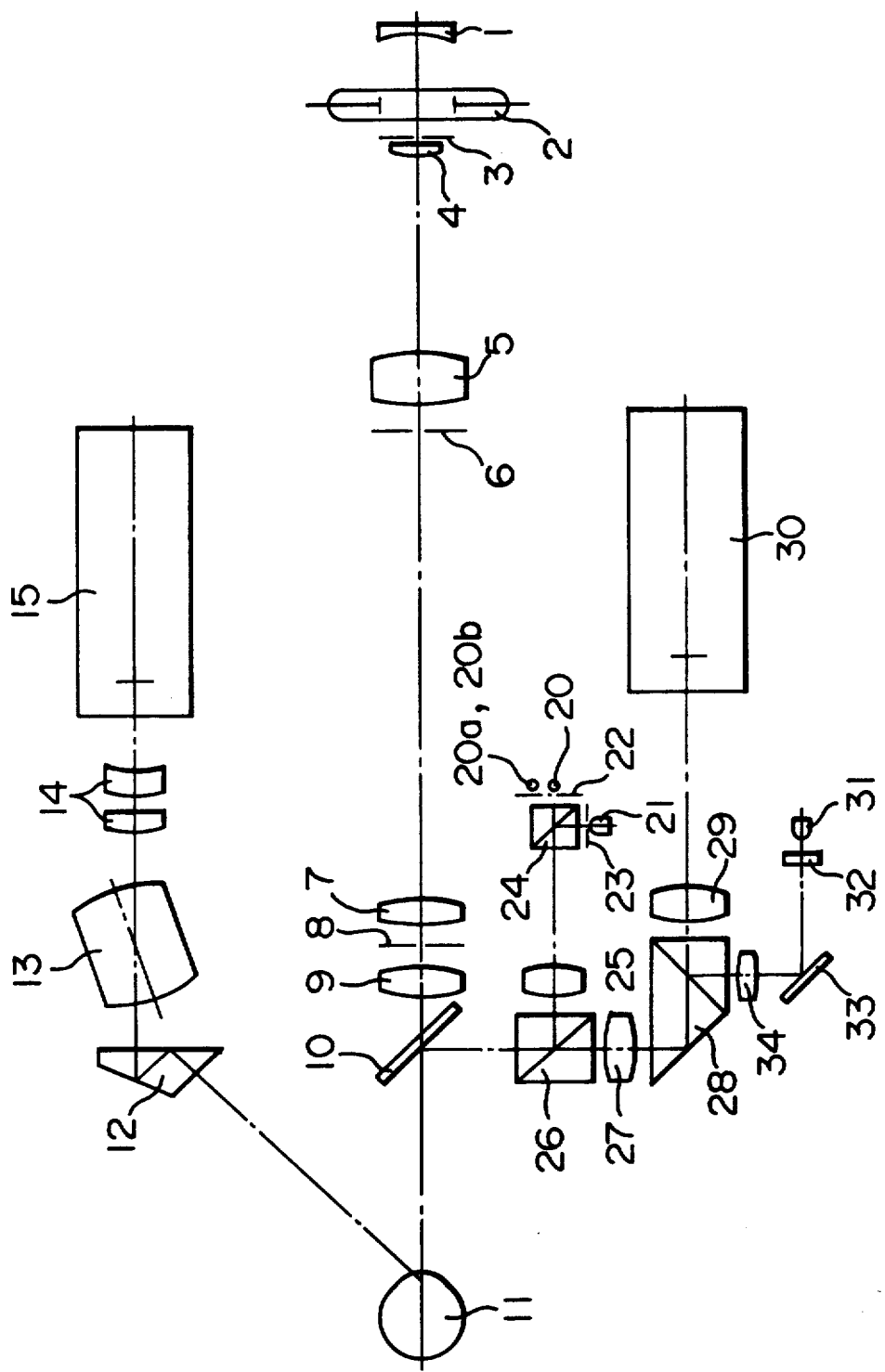
FIG. 1 is a schematic diagram showing an optical system of an apparatus for photography of the anterior segment of an eye of the present embodiment.

FIG. 1 is a schematic diagram showing an optical system of an apparatus for photography of the anterior segment of an eye. This optical system is constructed of a slit light projecting optical system, a slit section image photographing optical system, an alignment optical system, an illumination optical system for retroillumination photography and a retroillumination photographing optical system.

(a) Slit light projecting optical system

A reference numeral 1 indicates a reflecting mirror, and 2 indicates a xenon lamp light source for photographing a slit image. A xenon lamp is used in the present invention. However, it is not limited thereto, but it is also effectual to use a white laser light source and the like. Since direct scattering light of the slit projection light is photographed, scattering is larger as the wavelength gets shorter and detection capacity of the opacity area is increased, but white visible rays are preferable to be used because ultraviolet rays are injurious to eyeballs.

Numeral 3 indicates an aperture diaphragm, 4 and 5 indicate condenser lenses for leading a beam along an optical path, and 6 indicates a slit. This slit 6 passes the beam from the light source 2 while forming the beam into a fine slit form. Since an anterior chamber diameter is at approximately 13 mm though there is a difference among individuals, adjustment is made so that the slit image in the anterior segment of the eye becomes 14 to 15 mm in size.

Numerals 7 and 9 indicate objective lenses, and 8 indicates an aperture diaphragm, which limits the beam in a slit form. Numeral 10 indicates a dichroic mirror, which has a characteristic to pass the majority of visible rays and to reflect infrared rays. Numeral 11 indicates an eye to be examined.

The condenser lens 5 is arranged at a position where the aperture diaphragm 3 and the aperture diaphragm 8 have a conjugate relationship to thereof, and converges the light from the condenser lens 4. The objective lens 7 has a focal point at the position of the slit 6, and collimates the light passing through the slit 6 in parallel beams. The objective lens 9 is arranged so as to have a focal point in the anterior segment of a patient's eye 11, and has parallel beams passing through the slit 8 projected in the anterior segment of the patient's eye 11.

(b) Slit section image photographing optical system

A polarizing prism 12 changes the direction of the optical axis for the purpose of making the apparatus compact in size. Numeral 13 indicates a photographing lens, and numeral 14 indicates an anamorphic lens for correcting a distortion of an image. The anamorphic lens is constructed of a combination of cylindrical lenses (a toric lens being justifiable to be used, which is therefore included). Numeral 15 indicates a CCD camera.

A slit section image photographic optical system is arranged that the optical axis thereof inclines at 45° to the optical axis of the slit light projecting optical system. The photographing lens 13 is arranged to incline against the optical axis of the slit section image photographing optical system so as to satisfy Scheimpflug's principles. With such an optical arrangement, the slit section image formed on the CCD camera 15 can be focused throughout the section. It is also possible to arrange the photographing lens 13 perpendicularly to the optical axis and incline the image surface of the photographing optical system with respect to the optical axis, but a special camera is required in that case.

Besides, a distortion of an image photographed with the CCD camera remains even if the anamorphic lens 14 is used, but a main cause of the distortion of the image is due to the inclination of the photographing lens 13 based on the Scheimpflug's principles and the distortion may be expressed with a well-known expression. Thus, it is possible to eliminate the distortion of the image during picture image processing process. Further, it is also possible to eliminate all the distortions of the image during a picture image processing process without using the anamorphic lens 14.

It is possible to eliminate the corneal reflection to the slit section image photographing optical system by providing an eliminating plate (not shown) on the side of the photographing system between the patient's eye 11 and the dichroic mirror 10.

Besides, this apparatus is capable of photographing the anterior segment at two locations and more, and the slit portion has such a structure that 1 to 6 revolve as one body around the optical axis, and the slit section image photographing optical system has such a structure that 12 to 15 revolve interlocking with the slit revolution with the optical axis thereof.

(c) Alignment optical system

Numeral 20 indicates a light source for alignment, and is also used as a fixation light source for photographing the visual axis in the embodiment, thus emitting rays in the infrared region including visible rays partially.

Numeral 22 indicates a pin-hole plate, numeral 24 indicates a beam splitter, and numeral 25 indicates an alignment projection lens, and the alignment projection lens 25 has a focal point on the pin-hole plate 22, and forms the alignment light passing through the pin hole into parallel beams. Numeral 26 indicates a beam splitter and has a characteristic to transmit 50% of the beams and reflect 50% thereof in a 90 degree direction, with which the beam is made to have the same optical axis as a retroillumination photographing optical system and is projected to the eye to be examined.

The alignment light reflected on the cornea of the patient's eye is reflected by the dichroic mirror 10, transmits through the beam splitter 26, and an image is picked up with a CCD camera 30 having sensitivity in an infrared region through imaging lenses 27 and 29 and a prism 28 of the retroillumination photographing optical system described later.

Next, a reticle projecting system for performing alignment easily by using an corneal reflection image of the alignment light will be described.

A reticle projection light source 31 illuminates a ring-shaped reticle 32 from the back thereof, and a reticle image is reflected by a mirror 33. A reticle projection lens 34 has a focal point on the reticle 32. The reticle projection light is reflected by a prism 28 and becomes to have the same axis as the retroillumination photographing optical system, and forms a reticle image on a photographing plane of the CCD camera 30 through an imaging lens 29.

A ring-shaped reticle for alignment is used in the present embodiment, but not only a ring-shaped reticle, but also any reticle with which alignment is easy may be performed.

(d) Fixation visual target optical system

The light source 20 for alignment includes visible rays partially as described previously, and is also used as a fixation light source for photographing the visual axis.

Figure 2:
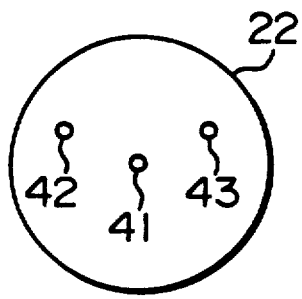
FIG. 2 is a front view showing a target for alignment.

In the present embodiment, in order to obtain a symmetrical image both in the case of photographing from a nose side and from an ear side in slit section image photographing, a fixation light source 20a for a right eye and a fixation light source 20b for a left eye which are separate from the light source 20 are provided so as to photograph while having the optical axis of the patient coincide with the photographing optical axis. Three pin holes are provided as the fixation targets on the pin-hole plate 22 corresponding to three pieces of light sources. FIG. 2 is a front view of the pin-hole plate 22, in which an alignment target 41 corresponds to the light source 20, a fixation target 42 for a right eye corresponds to the fixation light source 20a, and a fixation target 43 for a left eye corresponds to the fixation light source 20b.

Figure 3:
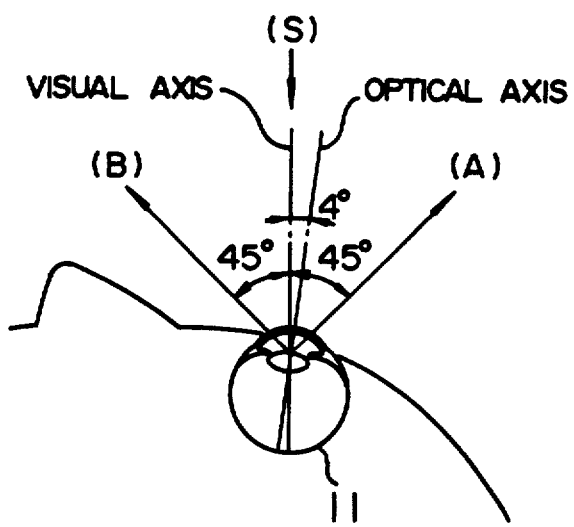
FIG. 3 is an explanatory view seeing a patient from the top.
Figure 4:
FIG. 4 shows sectional views thereof, in which (a) shows a picture image photographed from an ear side and (b) shows a picture image photographed from a nose side.
Figure 4:
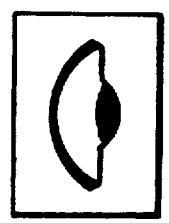

The reason why such a construction has been formed will be explained. FIG. 3 shows a view seeing the right eye of a patient from above. Here, mark (S) shows a slit projection optical axis, and shows the incident direction of the slit light. Marks (A) and (B) show the photographing directions on the ear side and on the nose side, respectively. Now, the photographed eye of the patient is in a state that the eye is fixed on the fixation target located on the slit projection optical axis. At this time, a section image including the visual axis is photographed. FIG. 4 shows sectional picture images, in which (a) is a picture image photographed from the nose side and (b) is a picture image photographed from the ear side. Both picture images are not symmetrical, and the picture image photographed from the ear side comes out better to show the interior of the crystalline lens. Such a situation is an obstacle to photograph the anterior segment of the eye at various angles and to conduct three-dimensional analysis of the anterior segment. The asymmetry of both picture images is caused by a fact that the eyeball points to the outside by approximately 4°. Namely, the visual axis and the optical axis of the eye do not coincide with each other as shown in FIG. 3, but the optical axis shifts toward the outside by approximately 4° and shifts downward by approximately 1° in an average for the Japanese though there is a difference among individuals, and the eyeball is rotationally symmetrical with respect to the optical axis. Accordingly, section photographing including the optical axis is made possible by determining the position of fixation taking the shift quantity from the visual axis into consideration.

An easily recognizable construction is preferable in such a manner that the fixation light sources 20a and 20b are made to flicker in order to distinguish them from the alignment target.

(e) Illumination optical system for retroillumination photography

An illumination light source 21 for retroillumination image photography emits infrared radiation. White light may be used for the illumination light for retroillumination image photography but infrared radiation is more preferable.

Here, the merit of using infrared radiation will be described.

When a patient's eye having thick opacity in a crystalline lens is photographed with retroillumination with white light, the contrast of an image is decreased. This is due to a fact that a part of incident light is scattered and reflected by the opacity areas and returns directly to the photographing system, and this light overlaps with the retroillumination image, thus causing decrease in contrast. Thereafore, it is necessary to reduce the light reflected by the opacity areas directly, which is solved by making the wavlength of the illumination light longer. That is, since the dimension of a protein particle in the opacity area is at several-tenth μm to several μm, infrared rays are deemed to be more difficult to be scattered. In addition, a photophobia feeling will never be given to a patient when infrared rays are used, thus making it possible to increase the quantity of light. Provided that the influence on scattering is reduced as the wavelength gets longer, but transmission of the reflection at the fundus gets better conversely and the opacity area becomes more difficult to be detected.

Accordingly, infrared rays having a wavelength at approximately 1 μm are preferable.

Numeral 23 indicates a pinhole, and numeral 24 indicates a beam splitter. The light becomes to have the same axis as the projection axis of the alignment light by means of the beam splitter 24.

The pin hole 23 is arranged at a focal point of a projection lens 25, and collimates the illumination light for retrolumination image photography from the pin hole 23 into parallel beams by the projection lens 25. The beam which is incident to the patient's eye is reflected at the fundus and retroilluminates a crystalline lens.

(f) Retroillumination photographing optical system

Numerals 27 and 29 indicate imaging lenses for photographing a retroillumination image, numeral 28 indicates a prism, and numeral 30 indicates a CCD camera for photographing a retroillumination image. The imaging lenses are arranged so that the photographing plane of the CCD camera 30 and a position of a virtual image by reflection of alignment light at the cornea become conjugate with each other.

In order to obtain a still more clear image, the corneal reflection is intercepted by providing a polarizing plate (not shown) having a polarizing axis meeting at right angles with the projecting system and the photographing system of infrared rays.

Sliding Mechanism of Optical System

The main body of the apparatus of the optical system composed of above-mentioned construction is housed in a casing. A sliding mechanism including of a movable table on which the main body of the apparatus is placed and a stationary table which moves the movable table relatively is provided, so that the main body of the apparatus housing the optical system is made movable back and forth and left and right together with the movable table by joy stick operation. The sliding mechanism used in the present embodiment is essentially the same as that which is known as a sliding rack of a measuring instrument for ophthalmology such as an refraction measuring instrument and a fundus camera, in which such a mechanism that the main body is moved longitudinally and horizontally by tilting the joy stick longitudinally and horizontally and is moved vertically by twisting and rotating the joy stick is adopted. Detailed description thereof is omitted herein.

Figure 5:
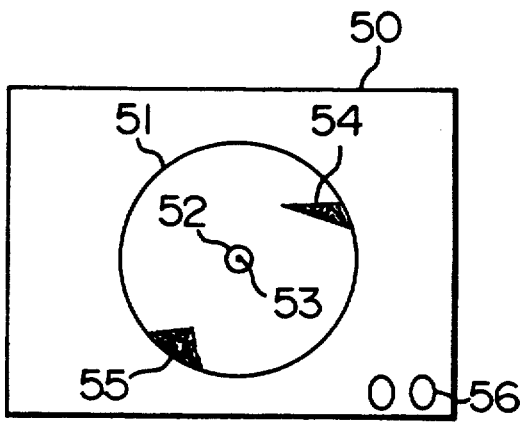
FIG. 5 is an explanatory view showing an example of a retroillumination image.

The movement of the main body in the optical axis direction which is made by the joy stick is detected by a potentiometer, and the displacement quantity from a reference position is controlled by a microcomputer and stored in a memory, and is also displayed on a monitor 50 (FIG. 5, numeral 56).

Figure 7:
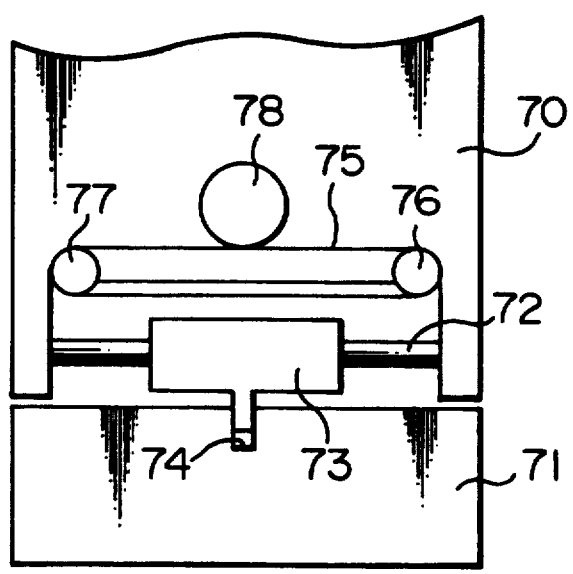
FIG. 7 is an explanatory view showing a mechanism for moving the main body in a longitudinal direction.

A detecting mechanism in the present embodiment will be described with reference to a sectional view taken along an optical axis direction shown in FIG. 7. In FIG. 7, the main body of the apparatus and the sliding mechanism in the optical system are omitted.

Numeral 70 indicates a movable table on which the main body of the apparatus housing the optical system is placed, and numeral 71 indicates a stationary table. A shaft 72 is provided in parallel with the optical axis direction on the movable table 70, and a bearing 73 is provided in a relatively movable manner in the axial direction of the shaft 72. A guide groove 74 is provided on the stationary table 71 so that the bearing 73 does not move in the detecting direction but is movable in the direction meeting at right angles with the detecting direction. A string 75 is provided on the bearing 73 for transmitting the movement quantity of the movable table 70, and the movement quantity is detected with a potentiometer 78 through pulleys 76 and 77.

Operation of the Apparatus

Next, the operation of the apparatus having a construction described above will be described.

(a) Slit section image photography

First, photographing of a slit section image including the visual axis of a patient's eye will be described.

In photographing, light which has transmitted through a pin hole 41 which is a target for alignment is projected to a patient's eye 11. An image reflected on the cornea of the pin hole 22 is formed on the light receiving face of the CCD camera 30 by imaging lenses 27 and 29. An operator performs alignment by moving the main body of the apparatus horizontally and vertically while watching the monitor 50 connected with the CCD camera 30 so as to put a corneal reflection image 53 into a small circle of a reticle image 52.

Further, alignment in the optical axis direction is set so that the corneal reflection image 53 becomes the smallest clear by moving the apparatus in a longitudinal direction.

Figure 6:
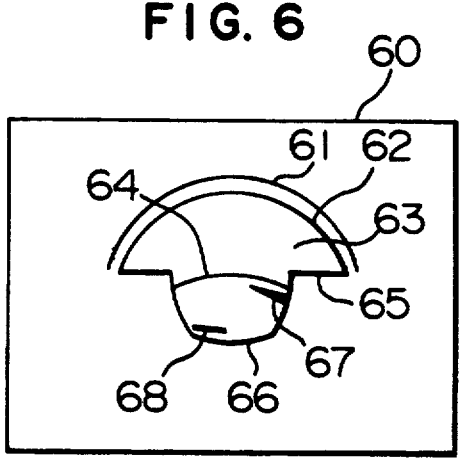
FIG. 6 is an explanatory view showing an example of a slit section image.

When alignment is completed by above-described operation, the light source 2 for photography is put ON, and the slit light is projected to the anterior segment of the patient's eye. The reflection at the anterior segment is projected onto a CCD camera 15 by a photographing lens 13 and an anamorphic lens 14, thus the slit section image being photographed. The photographed picture image is displayed on a monitor 60 connected with the CCD camera 15. FIG. 6 shows the photographed slit section image. In FIG. 6, numeral 61 indicates facies anterior corneae, 62 indicates facies posterior corneae, 63 indicates an anterior chamber, 64 indicates facies anterior lentis, 65 indicates an iris, and 66 indicates facies posterior lentis, 67 and 68 indicate opacity areas inside the crystalline lens.

Next, photographing along a slit section image including an optical axis of a patient's eye will be described.

In photographing, first, an image of the alignment target 41 is projected to the patient's eye 11. Further, when the patient's eye 11 is a right eye, the fixation light source 20a for a right eye is put ON, and the fixation target 42 is projected. At this time, the fixation light source 20b for a left eye is not put ON. (In case of a left eye, the fixation light source 20b is put ON for fixation at the fixation target 43.) The fixation targets 42 and 43 are made to flicker at this time for the purpose of distinguishing them from the alignment target 41.

When the patient's eye 11 stares at the fixation target 42 or 43, the photographing optical axis and the optical axis of the patient's eye coincide with each other. Thus, it is possible to photograph a slit section image including the axis of the patient's eye. The operation thereafter is the same as photographing a slit section image including the visual axis of the patient's eye.

(b) Retroillumination image photography

In case retroillumination image photography is performed, change-over to a retroillumination image photographing mode is made first. Alignment is made next, but this is the same as the case of slit photographing. Hence, the detail thereof is omitted herein.

The optical system is moved by operating a joy stick to a position where the corneal reflection image of the alignment light becomes the smallest. The corneal reflection image of the alignment light is formed while being shifted from the facies anterior corneae of the patient's eye toward the fundus side by ¼ of the radius of the corneal curvature. Since the image is formed at a fixed position from the facies anterior corneae for the same eye to be examined unless the radius of the corneal curvature changes largely, it may be adopted as a reference in the depth-measurement.

When a reset button is pushed after setting is made at a position where a luminescent spot reflected at a cornea for alignment becomes small and clear, taking that position as a reference position for the depth-measurement, a potentiometer 78 is operated. The measured depth on the monitor 50 is displayed at 0 at that time (FIG. 5, numeral 56). Thereafter, the movement quantity in the longitudinal direction of the main body by the joy stick is deteted by the potentiometer 78, and the movement quantity is displayed as the measured depth on the monitor 50.

Next, an illumination light source 21 for retroillumination image photography is put ON. When the illumination light source 21 for retroillumination image photography is put ON, the alignment light source 20 and the reticle projection light source 31 are put OFF at the same time.

The illumination light for retroillumination image photography becomes parallel beams at the projection lens 25 through the beam splitter 24 which are projected to the patient's eye. The light which has passed a transparent area of the patient's eye is reflected at the fundus, and retroilluminates the crystalline lens from the fundus side. Since the illumination light is scattered and absorbed in the opacity area of the crystalline lens, the transmitting light is reduced. The light from the patient's eye is reflected by the dichroic mirror 10, and forms an image on the light receiving face of the CCD camera 30 by means of imaging lenses 27 and 29 thereafter. A retroillumination image is displayed on the monitor 50 connected with the CCD camera 30.

Next, an operator places the apapratus at a desired position, setting to the depth to be photographed while watching the depth display on the monitor. When the photographing position is determined, a photographing button is pushed and the image is stored in a memory together with the value of the photographing position, and is also displayed on the monitor as a still picture.

Modification

The value of the depth recorded as the photographing position is a value obtained by measurement with the position at ¼ of the radius of curvature of the facies anterior corneae from the vertex corneae as the origin. However, it is more significant clinically to convert this value into a value of the depth from the vertex corneae or the facies anterior lentis.

For such a purpose, it is preferable to utilize a slit section image photographed with the present apparatus (see FIG. 6).

It is possible to obtain the distance between the vertex corneae and the luminous spot reflected at the cornea by conducting analysis of obtaining the radius of curvature of the facies anterior corneae from the slit section image. A simplest method of obtaining the radius of curvature is to select three points on the facies anterior corneae and obtain a point of intersection of perpendicular bisectors of two line segments formed with these points. There are a method known as the U.S. Pat. No. 4,019,813 and the like as the method of obtaining an exact radius of curvature from a corneal section image. Hence, the description thereof is omitted.

The distance between the cornea and the crystalline lens is also obtainable similarly from the analysis of a slit section image. Thus, it is possible to obtain the photographing depth of retroillumination image with the vertex corneae or the facies anterior lentis as the reference.

A method of projecting alignment light from the optical axis direction and setting the position of the corneal reflection image thereof at the reference point has been adopted in above-described embodiment. However, it is needless to say that another position such as the vertex corneae and the like may be adopted as a reference point by using another optical system such as a method that alignment light is projected from a symmetrical location out of the optical axis and the position of the coneal reflection image is detected so as to determine the position of the vertex corneae and a method that a detection pattern is projected from a different direction to the iris and the sciera for detection.

According to the present invention, it is possible to detect the photographing position of a retroillumination image exactly, and when chronological change is desired to obtain with respect to the same eye to be examined, it is possible to always form alignment at the same photographing position, thus making it possible to obtain a picture image of high quality. Further, it is possible to measure the extent of opacification exactly by photographing while changing the measured depth position.

What is claimed is:

1. A retroillumination image photographing apparatus for photographing of a crystalline lens of the eye in which an illuminating light is projected on an eye to be examined along an optical axis, and said crystalline lens of the eye is retroilluminated with reflected light at a fundus of the illumination light, comprising:

a photographing optical system;

alignment means for aligning said photographing optical system with a predetermined region of an eye to be examined;

storage means for storing an alignment position of said photographing optical system aligned by said alignment means, wherein a direction used for determining the alignment position is the direction of said optical axis;

origin computing means for determining a specific region of the eye to be examined as an origin of an image pickup position of said photographing optical system based on the alignment position stored by said storage means;

detecting means for detecting a movement quantity of said image pickup position of said photographing optical system; and display means for displaying said image pickup position of said photographing optical system based on the detection result of said detecting means.

2. A retroillumination image photographing apparatus as claimed in claim 1, wherein said alignment means which aligns said photographing optical system with a predetermined region of an eye to be examined consists of a projection optical system which projects onto a cornea in order to form an image reflected at the cornea, an observation system for observing the image reflected at the cornea, and a sliding mechanism which moves the retroillumination image photographing optical system in an optical axis direction, and that alignment is made by adjusting so that the image reflected at the cornea and the photographing optical system have a predetermined positional relationship.

3. A retroillumination image photographing apparatus as claimed in claim 1, wherein the origin computed with the origin computing means is at the position of the image reflected from a cornea.

4. A retroillumination image photographing apparatus according to claim 1, comprising an anterior eye segment section photographing system based on Scheimpflugs principles, and origin computing means adopting an origin of an image pickup position at a vertex cornea or a facie anterior lentis position, by analyzing an anterior segment sectional image photographed by said anterior eye segment section photographing system.

5. A retroillumination image photographing apparatus as claimed in claim 1, wherein said alignment means comprises a projection optical system which projects onto a cornea in order to form an image reflected at the cornea, an observation system for observing the image reflected at the cornea, and a sliding means for moving said photographing optical system in an optical axis direction, wherein alignment is achieved by adjustment of said sliding means so that the image reflected at the cornea and the photographing optical system have a predetermined positional relationship.

* * * * *